(12) United States Patent
Kim et al.

(10) Patent No.: US 11,786,190 B2
(45) Date of Patent: Oct. 17, 2023

(54) DENTAL LOW DOSE FLUOROSCOPIC IMAGE ACQUISITION DEVICE

(71) Applicants: Jae Hong Kim, Plano, TX (US); SungJin Jang, McKinney, TX (US)

(72) Inventors: Jae Hong Kim, Plano, TX (US); SungJin Jang, McKinney, TX (US)

( * ) Notice: Subject to any disclaimer, the term of this patent is extended or adjusted under 35 U.S.C. 154(b) by 286 days.

(21) Appl. No.: 17/220,120

(22) Filed: Apr. 1, 2021

(65) Prior Publication Data

US 2021/0307705 A1  Oct. 7, 2021

Related U.S. Application Data

(60) Provisional application No. 63/006,043, filed on Apr. 6, 2020.

(51) Int. Cl.
| | |
|---|---|
| *A61B 6/14* | (2006.01) |
| *A61B 6/00* | (2006.01) |
| *A61B 34/10* | (2016.01) |
| *G06T 7/00* | (2017.01) |

(52) U.S. Cl.
CPC .............. *A61B 6/145* (2013.01); *A61B 6/487* (2013.01); *A61B 6/542* (2013.01); *A61B 34/10* (2016.02); *G06T 7/0014* (2013.01); *A61B 2034/104* (2016.02); *G06T 2207/10016* (2013.01); *G06T 2207/10121* (2013.01); *G06T 2207/30036* (2013.01)

(58) Field of Classification Search
CPC ......... A61B 6/145; A61B 6/487; A61B 6/542; A61B 34/10; A61B 2034/104; A61B 6/06; A61B 6/4435; A61B 6/469; A61B 6/5205; A61B 2034/102; A61B 2034/105; A61B 2090/376; G06T 7/0014; G06T 2207/10016; G06T 2207/10121; G06T 2207/30036
See application file for complete search history.

(56) References Cited

U.S. PATENT DOCUMENTS

| 8,430,563 | B2 | 4/2013 | Uzbelger Feldman | |
| 2007/0280409 | A1* | 12/2007 | Konno | ............... G01T 1/249 |
| | | | | 378/19 |
| 2011/0150185 | A1 | 6/2011 | Uzbelger Feldman | |
| 2020/0138518 | A1* | 5/2020 | Lang | ..................... A61B 5/05 |
| 2020/0352530 | A1* | 11/2020 | Inglese | ............... A61B 6/4417 |

FOREIGN PATENT DOCUMENTS

WO    WO-2021105397 A1 *  6/2021  ............ A61B 6/145

* cited by examiner

*Primary Examiner* — David P Porta
*Assistant Examiner* — Mamadou Faye
(74) *Attorney, Agent, or Firm* — Byungjoo Park (57) ABSTRACT

Although the efficiency of fluoroscopy has always been well known in the Dental clinic, the extra-oral methods that were approached to realize it have always needed a large x-ray dose. This invention lowered the exposure of patient and operator at an extreme level by implementing an intraoral sensor of small area using multiple pickup binning that enhance pulsed x-ray and Signal to noise ratio (SNR) to lower the dose necessary for video. Additionally, it can be used efficiently in dental procedures by suggesting Guide Support Device that includes bite block and open block in between the sensor and emitter for an accurate and convenient scan.

12 Claims, 8 Drawing Sheets

Example of 3x3 multiple pickup binning and readout

Three groups of pixels = PixA, PixB, PixC

PixA = (A, F, H)
PixB = (B, D, I)
PixC = (C, E, G)

Read out frame of 3x3 multiple pickup binning 3n frame

3n+1 frame

3n+2 frame

DENTAL LOW DOSE FLUOROSCOPIC IMAGE ACQUISITION DEVICE

CROSS REFERENCE TO RELATED APPLICATIONS

This application claims priority under 35 U.S.C. § 119(e) to U.S. Provisional Patent Application No. 63/006,043 filed Apr. 6, 2020, which application is incorporated herein by reference.

BACKGROUND OF THE INVENTION

Existing dental fluoroscopic x-ray machines detect the x-ray image from outside of the patient's mouth, a large region of interest (ROI) is needed, which thus increases the amount of region exposed to the x-ray. Additionally, because a high dose of the x-ray is exposed toward the patient and the operator, the accumulated x-ray exposure amount toward the operator is considerably high. Our invention is created to improve both the convenience of fluoroscopic imaging, the stability of the low dose radiographic x-ray and to reduce patient and operator dose.

By using modern, highly sensitive imaging sensors, real-time digital imaging was able to be acquired; therefore, this kind of fluoroscopic technology improvement is used to help with accurate procedures. Furthermore, this invention uses a real-time image transmission technique in order to view the real-time image during the endodontic and implant procedure, which improves accuracy.

In addition, using a sensor optimized for the average size and depth of teeth, a small-sized collimated x-ray beam and low dose radiation pulse, the invention guides the patient and the operator to minimize dose.

In order to gain good quality x-ray image, some competitive technologies will raise Signal to noise ratio (SNR) by increasing the x-ray dose. The optimal method to improve image quality is to maintain SNR, while lowering dose. Also, for the emitter of pulse mode to gain an accurate low dose effect, the x-ray radiation pulse and the frame readout from the sensor need to be synchronized and an effective method for this should be provided.

BRIEF SUMMARY OF THE INVENTION

The invention that is being presented is a technology that has been made to minimize radiation exposure for patients and operators during both Endodontic and Implant procedures. Low dose real-time video technology is used to acquire the fluoroscopic image and Still Image in order to perform accurate Endodontic and Implant procedures, this includes a micro-control apparatus. Using the acquired image, the invention analyzes the Bone Density of the patient before an Implant procedure.

Especially, one method to get the minimum x-ray dose is doing real-time video at a more accurate position by applying Dental Fluoroscopic Intraoral Sensor (optimized for teeth size) and Small Beam Limit x-ray (collimator). Additionally, in order to overcome the limits of Dental Fluoroscopic Intraoral Sensor (optimized for teeth size) and Small Beam Limitation, the patient bites down on Micro Control Block and uses Micro Control Ball Joint Swivel to move freely to allow the invention to expose real-time video at various angles. So, the minimum x-ray dose is exposed using x-ray pulses, and the video is made by automatically sensing the x-ray radiation pulse from the sensor, and reading the sensor at the same frame rate. Like this, the x-ray radiation pulse and the sensor read must be synchronized for the low dose to work.

Moreover, during fluoroscopic procedures, when the frame rate is raised, SNR decreases. With current technologies, in order to maintain high quality imaging, x-ray dose must be increased. However, by using our invention, even though the frame rate is raised without increasing the x-ray dose, the SNR is enhanced because the sensor that applies real-time readout technique's algorithm minimizes the x-ray dose necessary for x-ray fluoroscopy while allowing real-time video.

BRIEF DESCRIPTION OF DRAWINGS

FIG. 1 is the side schematic of the Low Dose and High Image Quality Endodontic procedure according to the principle of this invention. As one method to acquire the minimum x-ray dose, it exposes real-time video at a more accurate position in order to overcome the limits of Dental Fluoroscopic Intraoral Sensor (optimized teeth size) and Small Beam Limitation, the patient bites down on Micro Control Block and uses Micro Control Ball Joint Swivel to move freely to allow the invention to expose real-time video in various angles.

FIG. 4 is a schematic of the Low Dose and High Image Quality Implant procedure. As one method to acquire the minimum x-ray dose, it exposes real-time video at a more accurate position and in order to overcome the limits of Dental Fluoroscopic Intraoral Sensor (optimized teeth size) and Small Beam Limitation, it uses 401 Block Guide and 402 Ball Joint Block for a more accurate real-time video during Implant procedure.

DETAILED DESCRIPTION OF THE INVENTION

Figure 1:
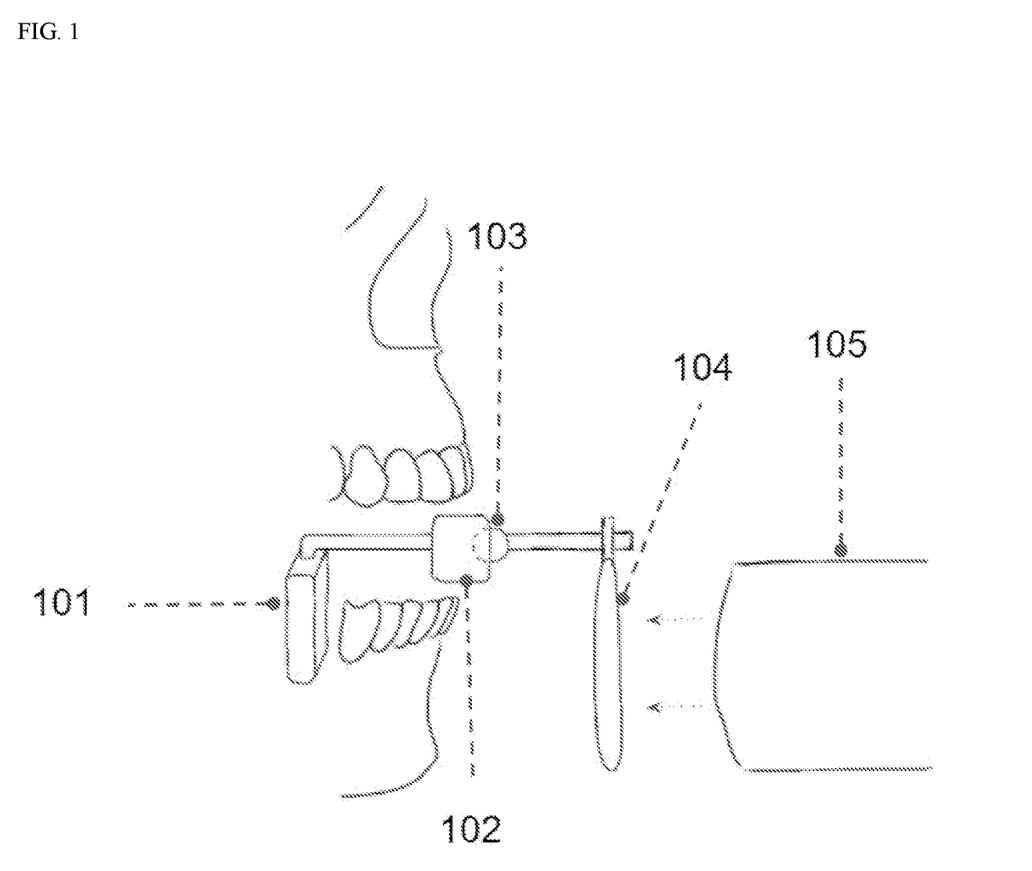
Figure 4:
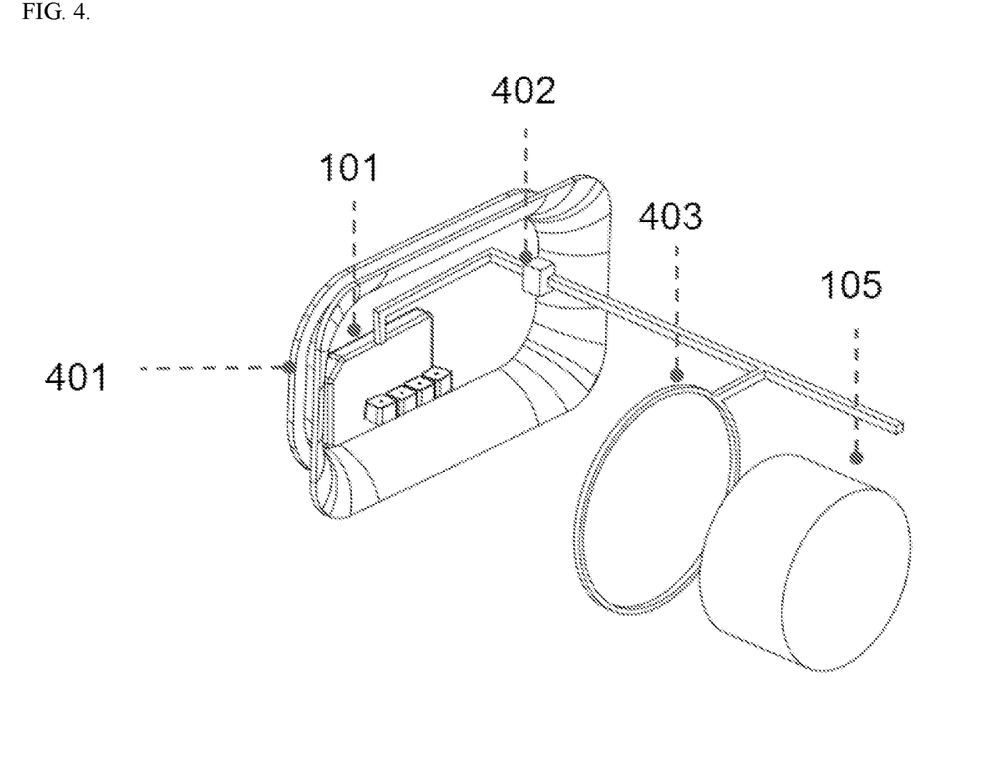

As it shows in FIGS. 1 and 4 during Endo and Implant procedure, 101 Dental Fluoroscopic Intraoral Sensor, 102 Micro Control Bite Block, 103 Micro Control Ball Joint Swivel, 104 X-ray Exposure Guide Ring, 105 Small Beam Limit X-ray Emitter, and 401 Open Block for Implant treatment make up the configuration to acquire the real-time image and still image.

For 101 Dental Fluoroscopic Intraoral Sensor, Low Dose and High Image Quality Real-time image and still image can be acquired by using CMOS, CCD, and A-SI TFT.101 Dental Fluoroscopic Intraoral Sensor.

102 Micro Control Bite Block plays an important role in positioning the exposure and has the function that allows it to allocate to the accurate position of Dental Fluoroscopic Intraoral Sensor.

103 Micro Control Ball Joint Swivel plays an important role in controlling the region of interest during exposure, and has the function that allows the control of Dental Fluoroscopic Intraoral Sensor and Small Beam Limit X-ray Emitter to be easy for the operator.

Because 105 the Small Beam Limit X-ray Emitter includes the pulse function of general continuous radiation, it plays an important role in acquiring Low Dose and High Image Quality real-time image and still image.

401 Open Block for Implant treatment plays the role of accurately positioning 101 Dental Fluoroscopic Intraoral Sensor and the patient's accurate position during Implant procedures.

The concept of the working process is when 105 Small Beam Limit X-ray Emitter exposes x-ray in a pulse method, 101 Dental Fluoroscopic Intraoral Sensor detects real-time video and still image and convert to digital image and then transmit it using Wi-Fi, Bluetooth, USB, Ethernet, Camera link to PC; the transmitted image goes through image processing and displays Fluoroscopic Image and Still Image.

Software provides real-time image and still image acquisition and display, storage, image processing, and measurement tool.

In case of acquiring an X-ray fluoroscopic image and still image such as the above method, because the operator exposes x-ray toward the patient, x-ray exposure for the operator is minimized.

To handle the difficulty of accurate controlling the position due to the small size of the sensor when exposing real-time video, the patient bites down on Micro Control Block and uses Micro Control Ball Joint Swivel to move freely and allow the invention to expose real-time video in various angles.

Figure 2:
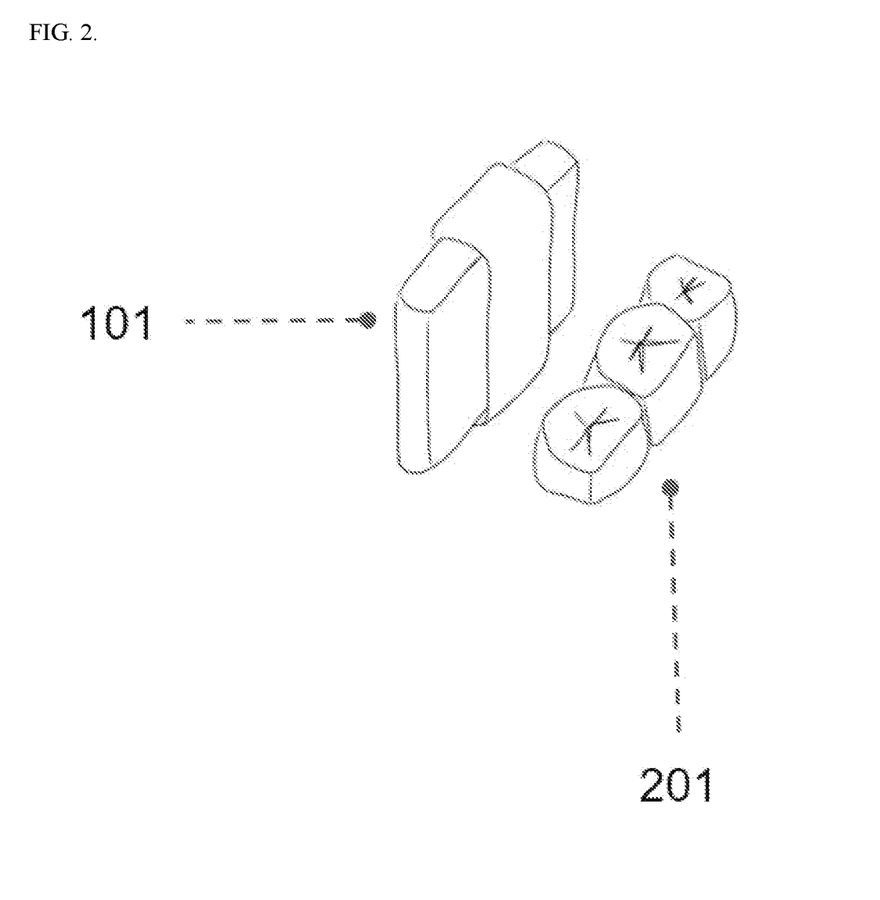
FIG. 2 is a side schematic of the Low Dose and High Image Quality Dental Fluoroscopic Intraoral Sensor according to the principle of this invention. As one method to get the minimum x-ray dose, out of the Fluoroscopic Image Acquisition Sensors, 101 Dental Fluoroscopic Intraoral Sensor is used as an intraoral insertion size.

As shown in FIG. 2, in order to acquire small Fluoroscopic Image and Still Image, a sensor that is small enough to be inserted intraoral needs to be used.

Figure 3:
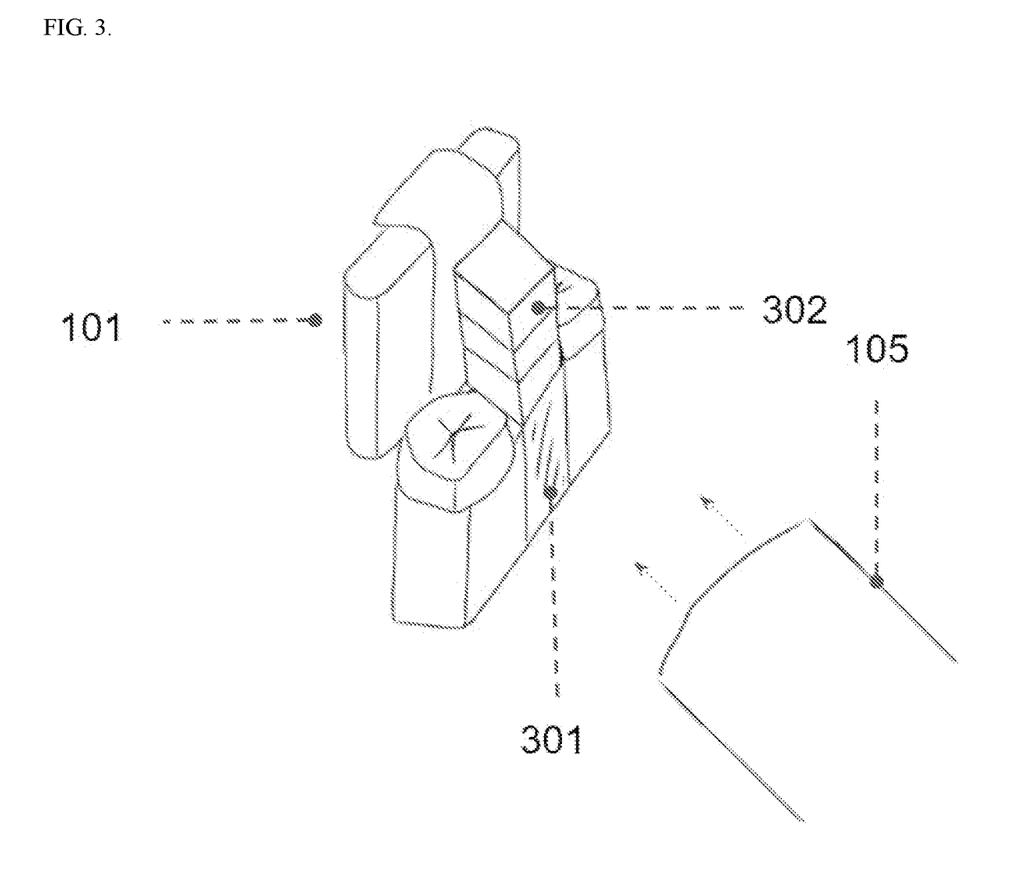
FIG. 3 is a schematic of the Low Dose and High Image Quality following the principle of this invention, which is for the Bone Density measurement. As a way to analyze the Bone Density of patient's gum before the Implant procedure, it is a method that measures the 301 Region of interest for Bone Density measurement by inserting 302 Compare Reference between the teeth, then exposing 105 Small Beam Limit X-ray Emitter, then comparing the Pixel Value of 301 Region of interest for Bone Density measurement and 302 Compare Reference from 101 Dental Fluoroscopic Intraoral Sensor to analyze the Bone Density. Compare Reference can be used for Acryl, Air, Teflon, Steel, Copper, SUS.

As shown in FIG. 3, As a way to analyze the Bone Density of patient's gum before the Implant procedure, it is a method that measures the 301 Region of Interest for Bone Density measurement by inserting 302 Compare Reference between the teeth, then exposing 105 Small Beam Limit X-ray Emitter, then comparing the Pixel Value of 301 Region of Interest for Bone Density measurement and 302 Compare Reference from 101 Dental Fluoroscopic Intraoral Sensor to analyze the Bone Density. Compare Reference can be used for Acryl, Air, Teflon, Steel, Copper, SUS.

Apply and measure the dual-energy x-ray absorptiometry method and reference compare method either individually or mixed to increase accuracy.

Software includes the function of measuring the Bone Density after placing Virtual Implant at the position of the region of interest.

As shown in FIG. 4 during Implant procedure, the concept of the working process is when 105 Small Beam Limit X-ray Emitter exposes x-ray in a pulse method, 101 Dental Fluoroscopic Intraoral Sensor detects real-time video and still image and convert to digital image and then transmit it using Wi-Fi, Bluetooth, USB, Ethernet, Camera link to PC; the transmitted image goes through image processing and displays Fluoroscopic Image and Still Image.

During the implant procedure, as one method to acquire the minimum x-ray dose, it exposes real-time video at a more accurate position and in order to overcome the limits of the dental fluoroscopic intraoral sensor (optimized teeth size) and small beam, it uses 401 Block Guide and 402 Ball Joint Block for a more accurate real-time video during the Implant procedure. After placing the virtual implant at the ROI's position, the operator references to the real-time virtual guide image of the software to make sure the hole in the patient's gum is drilled in the right direction.

The software displays the x-ray video acquired in 4 types of videos. The 4 types of videos displayed are individually Live Image, Hold Image, Virtual Adjustment image, and Rea-time Virtual Guide image, and these videos can be displayed either simultaneously or individually, and the software is able to control the position on the screen. Live Image displays the x-ray video acquired from Dental Fluoroscopic Intraoral Sensor in real-time.

Hold Image is a video out of those shown from Live Image that selects the still image that is able to allow careful observation of the ROI during Implant or Endo procedures. This Hold Image is either chosen automatically by the software or by the operator. This video can be more than one video, and out of the multiple Hold images, one is chosen and displayed.

Virtual Adjustment image is the implant's location and the nerve location and shape that is marked using the Hold image as a benchmark. When marking the location of the implant, the software displays using an already defined implant pattern or a simplified pattern, and this is either marked automatically in the software or directly by the operator.

Real-Time Virtual Guide image displays the Live image by overlaying the necessary guide information for the implant and endo procedure based on the marked information from Virtual Adjustment image. Procedures can be done accurately and safely using this information. For the Endo procedure, the File is inserted and checked by the naked eye while exposing real-time during nerve treatment to increase the accuracy.

If Implant is taken as an example, the following steps explain the process of video acquirement in the software.

1. 1st X-ray expose, Video is acquired at an adequate location intraoral. It checks if the location is adequate by viewing Live Image.
2. The video adequate for implant procedure is selected from Hold image.
3. The video selected from Hold image is sent to Virtual Adjustment image.
4. It marks where the implant will be located in the Virtual Adjustment image. If needed, it marks it by the nerve's location and shape.
5. 2nd x-ray expose is performed when drilling a hole for the implant. At this time, it checks if the hole is being drilled accurately using the guide shown in the Real-Time Virtual Guide Image. For the Endo procedure, the File is inserted and checked by the naked eye while exposing real-time during nerve treatment to increase the accuracy.

This invention's Dental Low Dose Fluoroscopic Image Acquisition Device is able to use not only fluoroscopic video, but also the radiographic exposure of conventional intraoral sensor. Radiographic image uses the conventional method of single x-ray expose and pulsed x-ray expose to acquire single image. If pulsed x-ray expose is used to acquire radiographic single image, the device image processes each frame from the fluoroscopic video to make single image. In this image processing, not only can calculations like adding, subtracting, dividing, and multiplying of each pixel be used, but also filters like mean, average, median, Gaussian, FFT, IFFT, pattern matching & detecting, edge detect & adjust, recursive, and digital noise recursive can be used.

Image Binning is a method of making fluoroscopic videos by combining the number of pixels according to the proper number row and column direction from the sensor. the number of pixels, which is determined by the row and column directions combined. The Image Binning is expressed as row×column. For example, 2×3 binning is combined 2 pixels in the row direction and 3 in the column directions. Therefore, it combines a total of 6 pixels to reconstruct as one pixel. In this reconstruction, sum, average, median methods are usually used.

As for conventional Binning, although the fluoroscopic video frame rate can be increased and the amplitude of fluoroscopic video signal can be raised by using the average of the combined pixels or the sum as one pixel, enhancement of Signal-to-Noise Ratio (SNR) cannot be expected. This is because the enhancement of SNR is difficult since in the case of summing 4 pixels from 2×2 binning, Noise and Signal of each pixel is summed together.

Furthermore, because Intraoral sensor is a high-resolution sensor with very small sized pixels, SNR is a very important factor for the quality of fluoroscopic videos. If the Intraoral sensor is applied as a fluoroscopic video, it is difficult to acquire enough x-ray exposure time to each pixel, and thus is a disadvantage for SNR.

Multiple pickup binning is an algorism used to maximize the fluoroscopic video's SNR while minimizing the x-ray exposure by binning selectively while circular rotating the pixels so that the pixels have the maximized x-ray exposure time possible.

Figure 5:
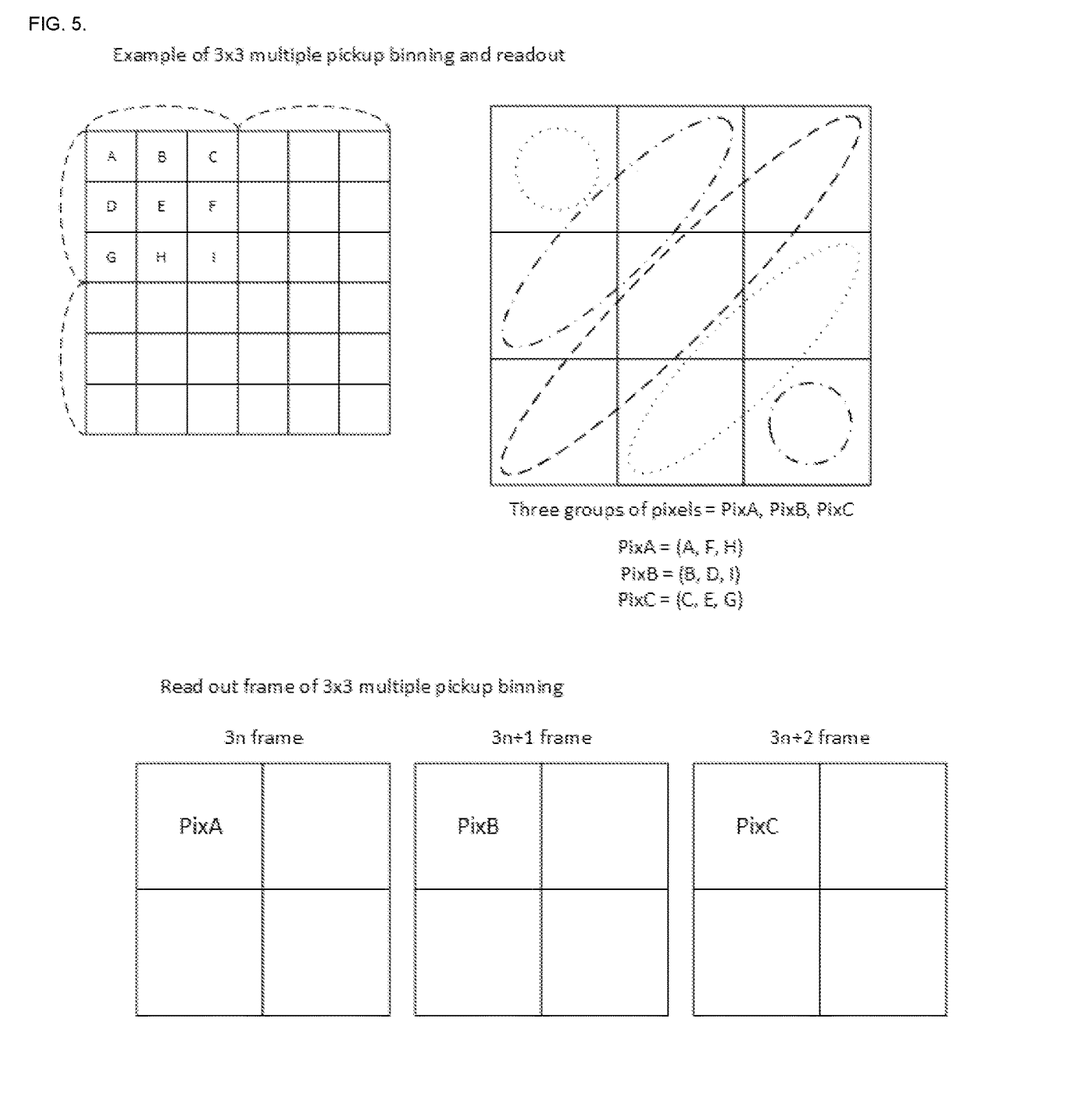
FIG. 5 shows 3×3 multiple pickup binning example.

Additionally, each binned pixel groups are divided into several subgroups. These groups are frame readout by circular rotation to acquire effects of frame rate increase and SNR improvement. This subgroup is called pixel element in this invention. Each pixel element can be chosen in a row, column, diagonal, or a random direction in the binned pixel group. Although the explanation for Multiple pickup binning was done in 2×2, but it can also be applied when binning by 3×3 in FIG. 5, 4×4, and etc.

Figure 6:
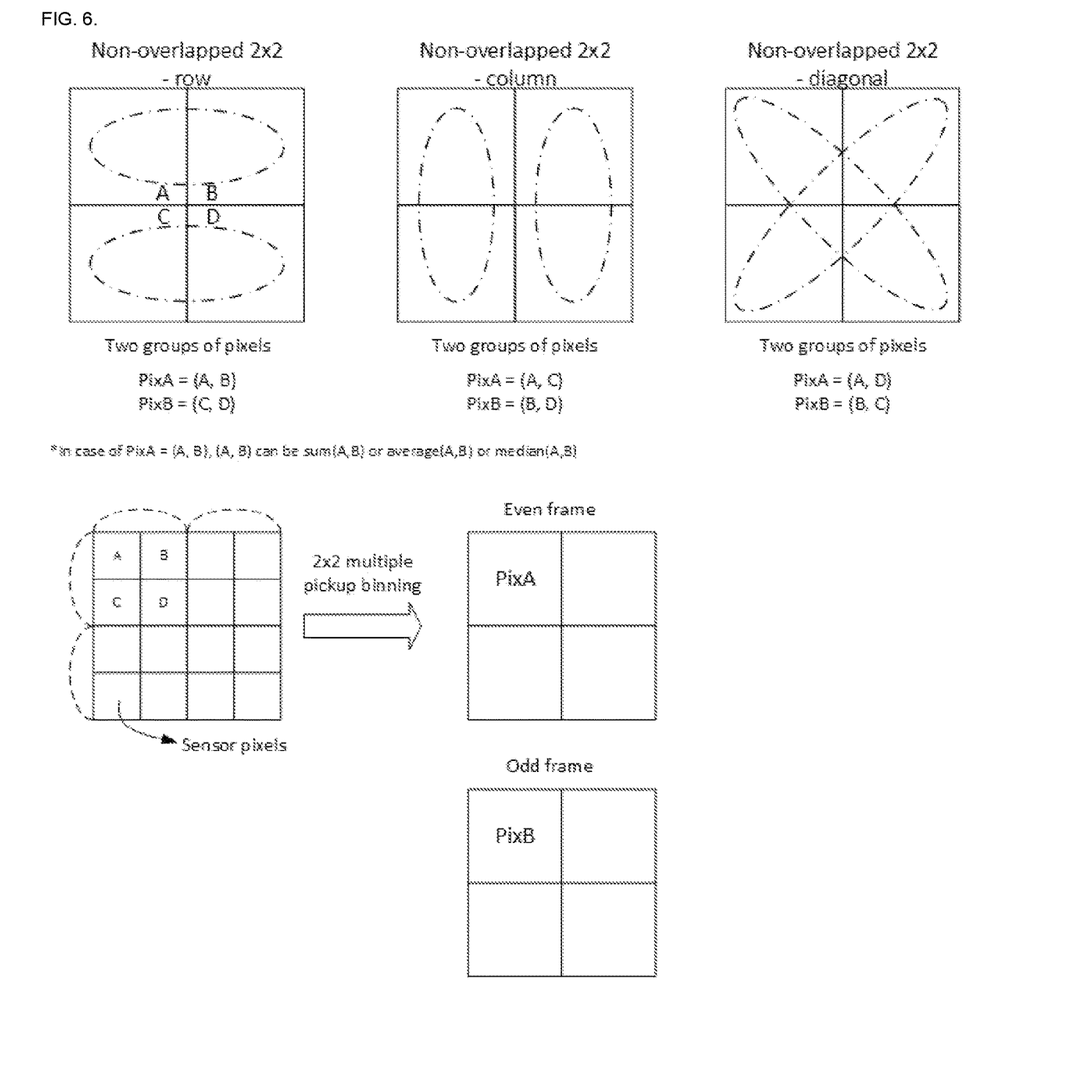
FIG. 6. shows Non-overlapped 2×2.
Figure 7:
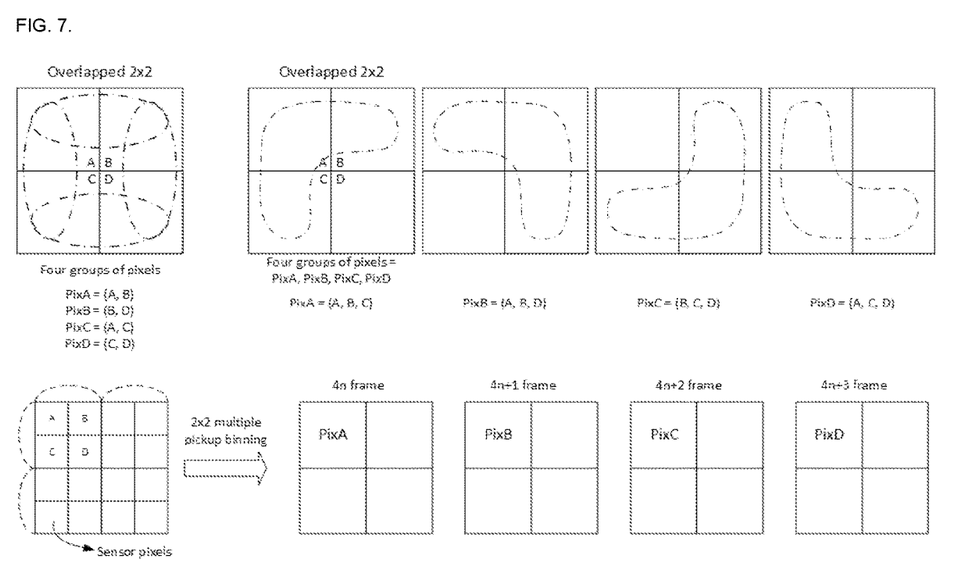
FIG. 7. shows Overlapped 2×2.
Figure 8:
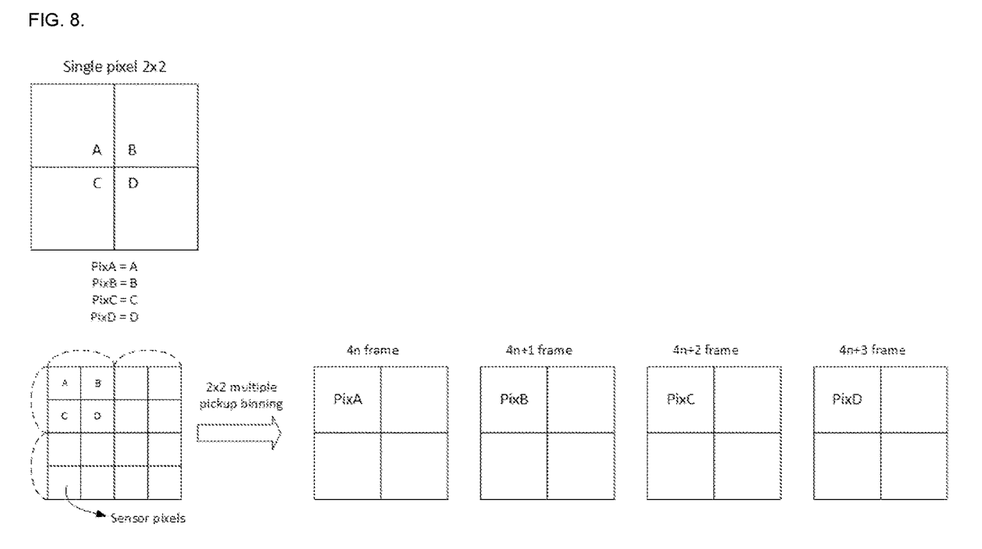
FIG. 8. shows Single pixel 2×2.

Multiple pickup binning uses three methods of "non-overlapped" in FIG. 6, "overlapped" in FIG. 7, and "single pixel" in FIG. 8.

In 2×2-non-overlapped-Multiple pickup binning, if the pixels inside each binned pixel group are called PixA, PixB, PixC, and PixD individually, they are divided into 2-pixel elements like (PixA, PixB), (PixC, PixD).

Out of the two-pixel elements divided, Multiple pickup binning reads out the first pixel elements to make fluoroscopic video even frame and then reads out the second pixel elements to make fluoroscopic video odd frame.

In other words, the second pixel element that will compose the odd frame is being exposed to x-ray while even frame's pixel element is being read. Also, the first pixel element is being exposed to x-ray while the odd frame's pixel element is being read.

If 2×2 binned pixel groups are read by distinguishing them into 2-pixel elements, the x-ray exposure time is doubled and the pixel Noise sum is halved compared to conventional binning. Because of this, the SNR can acquire enhanced videos.

2×2-non-overlapped-Multiple pickup binning's the video size becomes ¼ of the original, which allows the enhancement of the video's delivery speed by 4 times. Also, because it reads 1×2 groups by two-pixel elements, the fluoroscopic video frame rate can be enhanced by 2 times.

2×2-single pixel-Multiple pickup binning uses each pixel PixA, PixB, PixC, PixD as one-pixel element. Because it divides the 2×2 binned pixel group to be read in 4 times, it can make 4 fluoroscopic video frames.

In the 2×2-single pixel-Multiple pickup binning, the x-ray exposure time for each fluoroscopic video frame becomes about 4 times greater than conventional binning. In other words, the pixel of result fluoroscopic video frame has information as much as 1 of pixel Noise+quadrupled x-ray exposure time, which leads to the increase of SNR.

The size of video is also one-fourth the size of conventional binning and can enhance the fluoroscopic video frame rate by 4 times.

2×2-overlapped-Multiple binning makes a pixel element with 2 pixels by overlapping one pixel from the binned pixel group. In other words, pixel elements are configured as (PixA, PixB), (PixB, PixC), (PixC, PixD), (PixD, PixA) and are readout by circular rotation.

Because each pixel element configures one fluoroscopic video frame, 2×2-overlapped-Multiple pickup binning, which divides the 2×2 binned pixel group into 4-pixel elements to readout, can make 4 fluoroscopic video frame from 2×2 binned pixel group.

Compared to the Conventional binning, the overlapped pixel of 2×2-overlapped-Multiple pickup binning has one time the pixel Noise and x-ray exposure time, and the non-overlapped pixel of 2×2-overlapped-Multiple pickup binning has one time the pixel Noise and three times the x-ray exposure time.

Therefore, the pixel of 2×2-overlapped-Multiple pickup's fluoroscopic video frame can be seen as having 2 times the pixel's Noise and 4 times the x-ray exposure time information.

Although 2×2-overlapped-Multiple pickup binning has a small loss as for SNR compared to 2×2-non-overlapped-Multiple pickup binning, it has a major advantage of being able to raise the fluoroscopic video frame rate by 2 times.

For sensors that cannot x-ray expose for 4 times the time like 2×2-non-overlapped-Multiple pickup binning because they have small pixel Noise and are easily saturated, they can acquire good SNR and high fluoroscopic video frame rate if 2×2-overlapped-Multiple pickup binning is used.

Adaptive High Definite scan is a method that makes the fluoroscopic video by detecting x-ray and automatically syncing with the x-ray.

As for the Continuous x-ray, it detects the first x-ray exposure and readout from the sensor using the already defined fluoroscopic video frame rate, and then sends it to the PC.

If the X-ray is exposed using Pulse method, it detects each pulse of x-ray and readout from the sensor according to x-ray pulse rate and then sends it to the PC. In other words, it can make videos by automatically syncing the x-ray generator's pulse without wired connection.

Single x-ray expose detects x-ray exposure to readout the sensor and send it to PC. The x-ray expose time for single x-ray expose can get longer than Pulse. X-ray's detection has to be able to detect not only when the x-ray starts exposure, but also during exposure and after exposure.

X-ray detection uses the specific pixel value of the sensor, use an additional sensor to detect, or use the parasite capacitor component of pixel to detect.

LEGENDS

101. Dental Fluoroscopic Intraoral Sensor
102. Micro Control Bite Block
103. Micro Control Ball Joint Swivel
104. X-ray Exposure Guide Ring
105. Small Beam Limit X-ray Emitter
201. Teeth
301. Region of Interest for Bone Density measurement
302. Compare Reference for Bone Density Measurement
401. Open Block for Implant treatment
402. Micro Control Ball Joint Swivel
403. X-ray Exposure Guide Ring

What is claimed is:

1. A method for dental low dose fluoroscopic image acquisition, the method comprising:
    using a low dose radiation in a real time video technique to acquire a fluoroscopic image and a still image to perform dental procedures;
    exposing the low dose radiation in the real time video at a position in order to overcome limitations of a dental fluoroscopic intraoral sensor and small beam limitations;
    having a patient bite down on a micro control block;
    controlling a micro control ball joint swivel to be exposed to the low dose radiation in the real-time video;
    using the dental fluoroscopic intraoral sensor;
    irradiating a small-sized collimated x-ray beam to a region of interest image;
    exposing the low dose radiation with a pulse method;
    measuring the region of interest image for bone density measurement with a compare reference between the teeth;
    exposing a small beam limit x-ray emitter;
    comparing a pixel value of the region of interest image for bone density measurement and the compare reference from the dental fluoroscopic intraoral sensor to analyze the bone density; and
    high image quality implant procedure.

2. The method of claim 1, wherein the dental fluoroscopic intraoral sensor is optimized for teeth size.

3. The method of claim 1, wherein the compare reference includes:
    Acryl; Air; Teflon; Steel; Copper; and SUS.

4. A method of making fluoroscopic videos, the method comprising:
    combining a number of pixels according to a proper number of row and column direction from a sensor and expressing an image binning as row×column;
    combining 2×2 binning 2 pixels in a row direction and 2 pixels in a column direction;
    combining a total of 4 pixels to reconstruct as one pixel;
    using a multiple pickup binning algorism to maximize a fluoroscopic video's signal-to-noise ratio (SNR);
    dividing into a subgroup from each binned pixel group;
    reading out a first pixel element to make a fluoroscopic video even frame;
    reading out a second pixel element to make a fluoroscopic video odd frame.

5. The method of claim 4, wherein to reconstruct is sum, average, or median method.

6. The method of claim 4, wherein the multiple pickup binning comprising: non-overlapped; overlapped; and single pixel.

7. The method of claim 4, wherein each binned pixel group comprising: PixA; PixB; PixC; and PixD.

8. The method of claim 6, wherein the non-overlapped is 2×2 non-overlapped multiple pickup binning divided into a subgroup from each binned pixel group.

9. The method of claim 8, wherein the subgroup is 2-pixel elements (PixA, PixB), (PixC, PixD).

10. The method of claim 6, wherein the overlapped is 2×2 overlapped multiple pickup binning divided into a subgroup from each binned pixel group.

11. The method of claim 10, wherein the subgroup is 2-pixel elements comprising: (PixA, PixB); (PixB, PixC); (PixC, PixD); and (PixD, PixA).

12. The method of claim 6, wherein the single pixel is 2×2-single pixel multiple pickup binning divided into a subgroup from each binned pixel group.

* * * * *